United States Patent [19]

Garren et al.

[11] Patent Number: 4,899,747

[45] Date of Patent: Feb. 13, 1990

[54] METHOD AND APPARTUS FOR TREATING OBESITY

[76] Inventors: Lloyd R. Garren; Mary L. Garren, both of P.O. Box 3738, Wilmington, Del. 19807

[21] Appl. No.: 529,609

[22] Filed: Sep. 6, 1983

Related U.S. Application Data

[63] Continuation-in-part of Ser. No. 329,182, Dec. 10, 1981, Pat. No. 4,416,267.

[51] Int. Cl.$^4$ .............................................. A61B 17/00
[52] U.S. Cl. ...................................... 606/192; 604/96; 604/103
[58] Field of Search ............... 128/1 R, 344, 346, 325, 128/303 R, 128, 897; 604/93, 96-97, 101-103, 49, 54

[56] References Cited

U.S. PATENT DOCUMENTS

| | | | |
|---|---|---|---|
| 1,690,995 | 11/1928 | Pratt | 128/344 |
| 4,018,230 | 4/1977 | Ochiai et al. | 128/344 |
| 4,083,369 | 4/1978 | Sinnreich | 128/344 X |
| 4,085,757 | 4/1978 | Pevsner | 604/96 X |
| 4,102,342 | 7/1978 | Akiyama et al. | 128/325 |
| 4,133,315 | 1/1979 | Berman et al. | 604/96 X |
| 4,134,405 | 1/1979 | Smit | 128/303 R |
| 4,246,893 | 1/1981 | Berson | 128/346 X |
| 4,311,146 | 1/1982 | Wonder | 128/344 X |
| 4,315,509 | 2/1982 | Smit | 128/303 R |
| 4,416,267 | 11/1983 | Garren et al. | 128/1 R |
| 4,485,805 | 12/1984 | Foster, Jr. | 128/344 X |

FOREIGN PATENT DOCUMENTS

| | | |
|---|---|---|
| 2822925 | 11/1979 | Fed. Rep. of Germany. |
| 0000007 | 1/1980 | PCT Int'l Appl. ............ 604/96 |
| PCT/US79/-00354 | 1/1980 | PCT Int'l Appl. . |

OTHER PUBLICATIONS

Kurze Mitteilung, A. E. Hennig, "Ambulant Weight Loss by a Ballon Placed in the Stomach", Im. Med. 6, 149-152 (1979).
Kleine Mitteilungen: DMW 1982, 107. Jg., No. 9, p. 360, "Fattisch" & translation.
DMW 1982, 107.Jg., No. 37, p. 1413, "Der Magenballon in der Behandlung der Adipositas" & translation.
DMW 1982, 107.Jg., No. 49, p. 1904 "Intragrastrische Ballons" & translation.

Primary Examiner—Angela D. Sykes
Attorney, Agent, or Firm—Connolly & Hutz

[57] ABSTRACT

A stomach insert for treating obesity in humans by reducing the stomach volume comprises a flexible, free floating and unattached, inflatable balloon, the balloon being inflatable to a volume effective to reduce the stomach volume of a person being treated. At least a portion of the balloon has a self-sealing substance to facilitate puncture thereof with insufflation means through which the balloon is inflated and to facilitate sealing of the puncture upon removal of the insufflation means. The method herein comprises positioning the balloon inside the stomach of the person being treated for obesity so as to reduce the stomach volume.

13 Claims, 3 Drawing Sheets

METHOD AND APPARTUS FOR TREATING OBESITY

CROSS REFERENCE TO RELATED APPLICATION

The present application is a continuation-in-part of application Ser. No. 329,182 filed Dec. 10, 1981, now U.S. Pat. No. 4,416,267.

BACKGROUND OF THE INVENTION

The present invention relates to a medical treatment of obesity in humans, and more particularly to both apparatus and method for curbing the appetite of persons being treated for obesity.

Extreme obesity is a major illness in the United States and other countries. Its complications include hypertension, diabetes, coronary artery disease, stroke, congestive heart failure, venous disease, multiple orthopedic problems and pulmonary insufficiency with markedly decreased life expectancy. Medical management including dietary, psychotherapy, medications and behavioral modification techniques have yielded extremely poor results in multiple trials. Several surgical techniques have been tried which have bypassed the absorptive surface of the small intestine or have been aimed at reducing the stomach size by either partition or bypass. These procedures have been proven both hazardous to perform in morbidly obese patients and have been fraught with numerous life-threatening postoperative complications. Moreover such operative procedures are often difficult to reverse.

Non-surgical approaches for the treatment of obesity include voluntary dieting which is often unsuccessful since most persons do not possess sufficient willpower to limit the intake of food. Other approaches include the use of stomach fillers such as methyl cellulose, often taken in the form of tablets. The methyl cellulose expands in the stomach leaving the person with a filled-up feeling. Also, inflatable bag and tube combinations have been proposed wherein the bag is swallowed into the stomach and the tube attached thereto is used to periodically inflate the bag, particularly just prior to mealtime or during the meal. Once the person has eaten, the bag can be deflated all at once, or it can be deflated gradually over a period of a few hours so as to simulate the condition of digestion occurring and the gradual reduction of stomach contents.

U.S. Pat. No. 4,133,315 granted Jan. 9, 1979 discloses such an inflatable bag and tube combination. The tubing remains attached to the bag and inside the esophagus of the person being treated. These tubes are often the cause of erosions and ulcerations of the esophagus. This patent also discloses a gastrotomy method wherein the permanently attached tube used to distend the stomach bag extends through an opening in the stomach wall as well as an opening in the abdomen.

Also, U.S. Pat. No. 4,246,893 granted Jan. 27, 1981 discloses an inflatable bag and tube combination which is surgically positioned outside and adjacent to the stomach. Upon inflation of the bag the upper abdomen is distended and the stomach compressed to thereby produce a sense of satiety which reduces the person's desire to ingest food.

Hence, reducing the size of the gastric compartment has been shown to induce weight loss in a significant percentage of people, and the present invention is aimed at a device which non-operatively reduces the size of the gastric compartment and which is easily removed.

SUMMARY OF THE INVENTION

Accordingly, it is an object of the present invention to treat obesity by curbing a person's appetite in a manner which is safe, convenient and effective.

Another object of the present invention is to treat obesity by effectively reducing the stomach volume of the person being treated.

In accordance with the present invention, a stomach insert for treating obesity in humans by reducing the stomach volume comprises a flexible, free-floating and unattached, inflatable balloon, the balloon being inflatable to a volume effective to reduce the stomach volume of a person being treated. At least a portion of the balloon has a self-sealing substance to facilitate puncture thereof with insufflation means through which the balloon is inflated and to facilitate sealing of the puncture upon removal of the insufflation means.

Preferably, the stomach balloon has an inflated volume of approximately 200 to 800 cc., and the material from which it is made is both soft and flexible, having significant strength to resist over-inflation.

The method for treating obesity in humans according to the present invention comprises the steps of assembling a deflated stomach balloon with an insufflation tube releasably attached thereto inside a standard stomach tube. Thereafter the stomach tube is introduced through the mouth and into the stomach, and the balloon is urged out of the stomach tube into the stomach compartment. The attached insufflation tube is then used to inflate the balloon with a given amount of fluid. Finally, the insufflation tube is detached from the inflated balloon and along with the stomach tube removed from the body of the person. Usually the balloon is inflated to a volume approximately 80% of the stomach volume.

The balloon may be removed from the stomach by introducing extraction means through the mouth and into the stomach, grasping and puncturing the balloon with the extraction means, and then withdrawing the deflated balloon out of the stomach and through the mouth. The extraction means may include a fiberoptic gastroscope with needle biopsy forceps.

Also, an assembly is provided comprising a stomach tube having a slit at the inner end thereof. A deflated stomach balloon is inside the tube at the inner end and a releasable drawstring closes the tube at the slit. Once the tube is in the stomach, the drawstring is removed and the balloon inflated. The balloon is easily separated from the tube as the tube spreads apart at the slit.

BRIEF DESCRIPTION OF THE DRAWINGS

Novel features and advantages of the present invention in addition to those mentioned above will become apparent to those skilled in the art from a reading of the detailed invention in conjunction with the accompanying drawings wherein similar reference characters refer to similar parts and in which.

3

Figure 4:
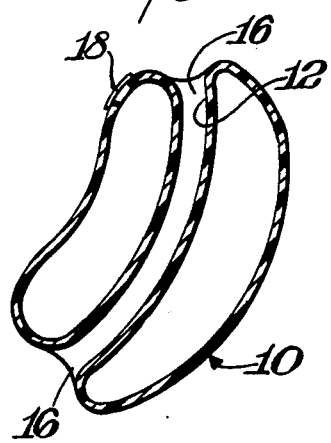
Figure 3:
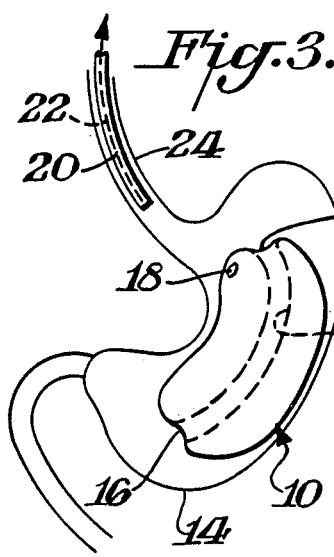
Figure 5:
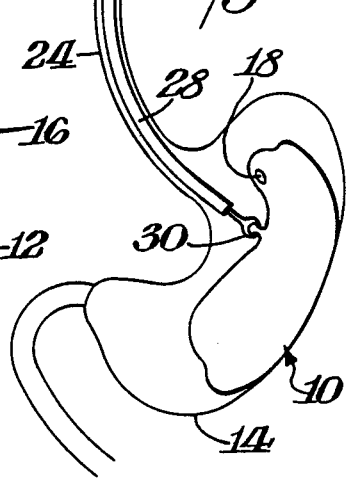
Figure 6:
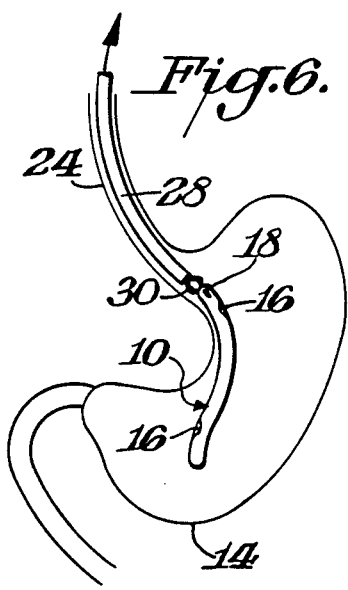
Figure 7:
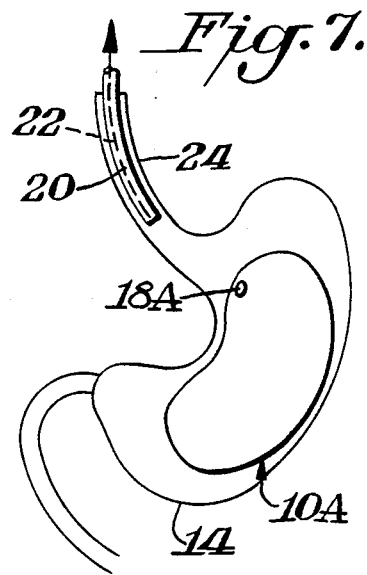
Figure 8:
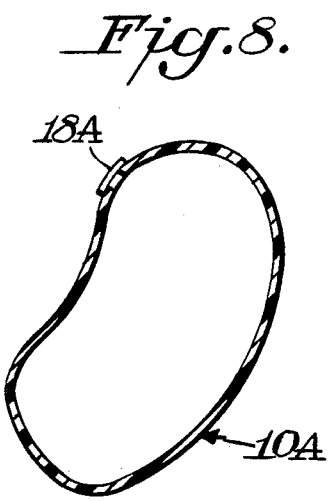
Figure 9:
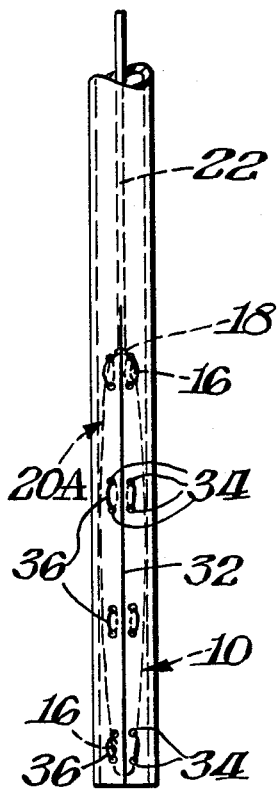
Figure 10:
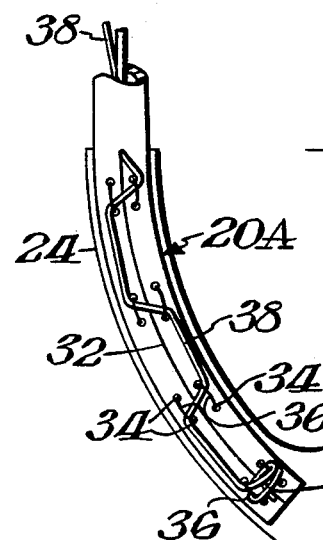
Figure 11:
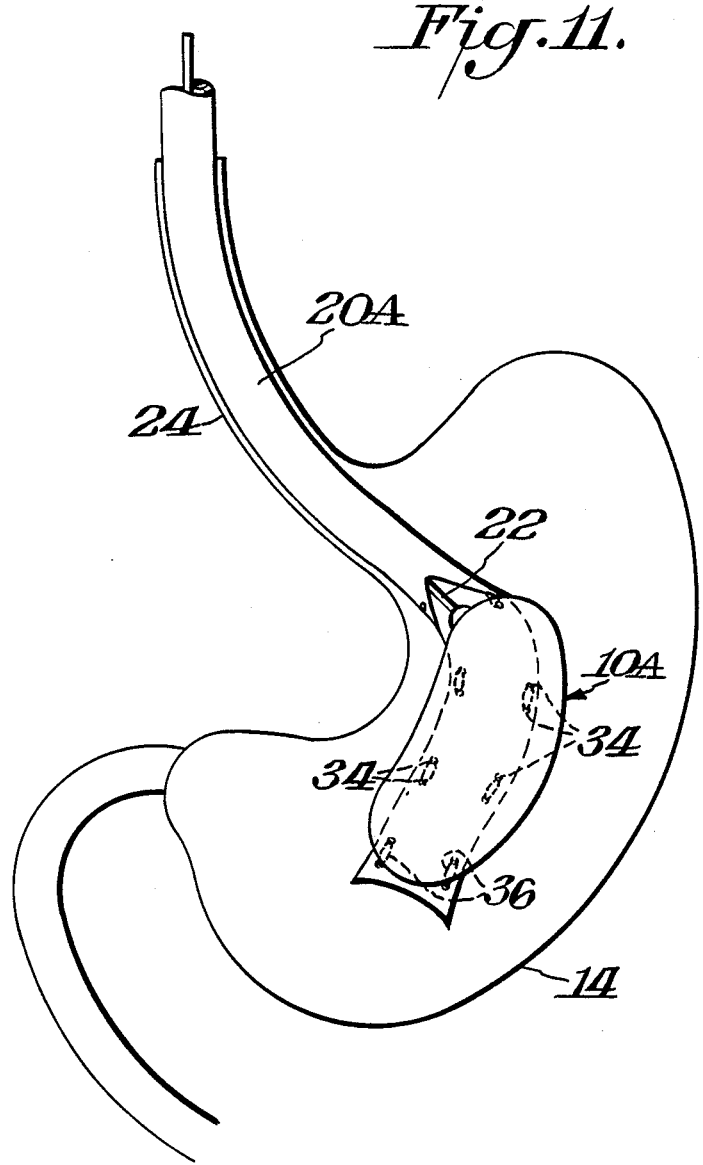

FIG. 3 is a schematic side elevational view of the balloon fully inflated inside the stomach with the insufflation tube detached from the balloon and both tubes being withdrawn from the person;

FIG. 4 is a cross-sectional side elevational view of the fully inflated balloon shown in FIG. 3;

FIG. 5 is a schematic side elevational view of a fiberoptic gastroscope with needle biopsy forceps extending therefrom in the process of puncturing and removing the balloon from the stomach;

FIG. 6 is a schematic side elevational view similar to FIG. 5 with the balloon fully deflated and ready for removal;

FIG. 7 is a schematic side elevational view similar to FIG. 3 but illustrating an alternate embodiment of the stomach balloon;

FIG. 8 is a cross-sectional side elevational view similar to FIG. 4 illustrating the stomach balloon of FIG. 7;

FIG. 9 is a side elevational view of an alternate stomach tube according to the present invention with the deflated balloon and its insufflation tube disposed therein;

FIG. 10 is a schematic side elevational view of the stomach tube of FIG. 9 about to enter the stomach; and FIG. 11 is a view similar to FIG. 10 with the balloon partially inflated inside the stomach.

DETAILED DESCRIPTION OF THE INVENTION

Referring in more particularity to the drawings, FIGS. 1-6 herein illustrate a stomach implant or insert for treating obesity in humans by reducing the stomach volume. Specifically, the stomach insert comprises a flexible torus-shaped inflatable balloon 10 having a central opening 12 extending therethrough. The balloon may be fabricated from medical grade rubber or synthetic rubber-like material, one criteria being that such material be impervious so that the balloon is capable of holding a charge of air or other fluid. Balloon 10 comprises a single layer, as shown best in FIG. 4. Obviously, the material selected must be capable of surviving in the gastric compartment, and not extract (give off) or absorb (take in). It should be soft and flexible having significant dynamic strength to resist over-inflation. As such, the finished product will inflate to the manufactured shape and not further. Moreover, the finished product may be formed from a flat sheet of material and fastened together by solvent, heat, or RF welding techniques. One specific material is TUFTANE, polyester base, thermoplastic, polyurethane film manufactured by the Lord Corp.

As explained more fully below, the central opening 12 provides a passageway for solids and liquids as they pass through the stomach cavity 14. As shown best in FIG. 4, the central opening 12 includes flared outer ends 16 that function to provide wide entrances to the central opening.

Continuing, the balloon 10 includes an injection site 18 fabricated from any self-sealing substance such as used in the injection site of standard intravenous tubing. The injection site 18 serves as a location for inflation of the balloon 10, and the balloon is sized so that its inflated volume is approximately 200 to 800 cc.

A standard levine or stomach tube 20 is utilized to position the balloon 10 inside the stomach. Also, prior to positioning the balloon inside the stomach, an insufflation tube 22 in the form of small bore polyethylene tubing is attached to the deflated balloon. In this regard the free end of the insufflation tube may carry a needle 26 which punctures the balloon at the injection site 18. As shown best in FIG. 1, the deflated stomach balloon 10 with the insufflation tube 22 attached thereto are stored inside the stomach tube 20 just prior to introducing the stomach tube through the mouth and into the stomach of the person being treated for obesity. The procedure is as follows.

Figure 1:
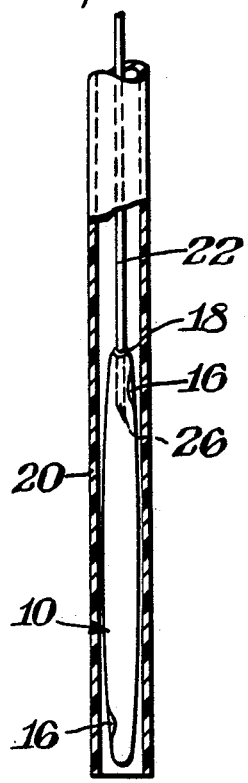
FIG. 1 is a side elevational view of a stomach tube according to the present invention partially broken away to show details of the deflated balloon and its insufflation tube.
Figure 2:
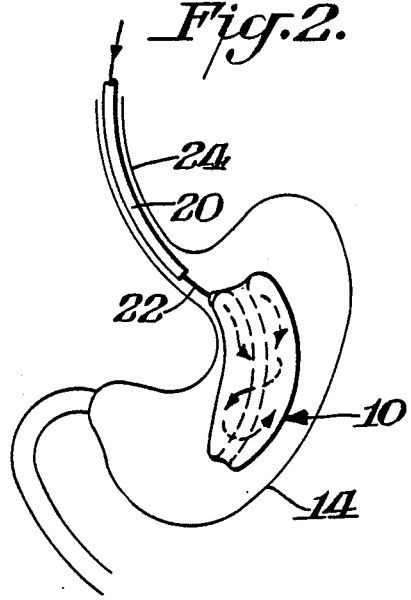
FIG. 2 is a schematic side elevational view illustrating the balloon outside the stomach tube and partially inflated into the stomach.

Once the components are assembled as shown in FIG. 1, the stomach tube is fed through the mouth and esophagus 24 into the stomach cavity 14. Next, the insufflation tube 22 is urged inwardly relative to the stomach tube 20 to thereby position the deflated balloon 10 inside the stomach. Air or another fluid is then introduced into the balloon 10 via the insufflation tube 22, as shown in FIG. 2. After the balloon is inflated to approximately 80% of the stomach volume, the needle end 26 of the insufflation tube is removed from the injection site 18 which self-seals after such removal. The needle 26 is then housed inside the stomach tube and the stomach tube then withdrawn from the body of the person leaving a free-floating and unattached balloon.

The inflated bag is positioned as shown in FIG. 3 with the central opening therein serving as a passageway through the stomach for both liquids and solids. Also, since the balloon is free-floating liquid and solid foods pass around the exterior surface of the balloon between that surface and the interior of the stomach wall. As noted above, the balloon is inflated to a volume of approximately 80% of the stomach volume and this phase of the procedure may be accomplished with the aid of x-ray examination, for example. The balloon remains in the stomach for the period the person is being treated for obesity, perhaps a period of three months or more, and it functions to reduce the volume size of the stomach and thereby curb the appetite of the person being treated for obesity.

Upon completion of the treatment, the balloon is easily removed from the stomach by means of a fiberoptic gastroscope 28 with needle biopsy forceps 30. As shown in FIG. 5, the needle biopsy forceps grasp and puncture the ballon 10, and once the balloon is fully deflated it is simply drawn out of the stomach into the esophagus and out through the mouth of the person being treated.

FIGS. 7 and 8 illustrate an alternate embodiment of the invention that includes a stomach insert or balloon 10A similar in all respects to balloon 10 except for the absence of the central opening or passageway. As shown best in FIG. 8, balloon 10A comprises a single layer. Also, as with balloon 10, the embodiment 10A of FIG. 7 and 8 has a preshape and the finished product inflates to such manufactured shape and not further. Balloon 10A has an oblong shape and includes an injection site 18A for the same purpose as site 18 of insert 10. The insert 10A is made of the same materials as insert 10. Also, it is positioned in the stomach, inflated, and removed in the same manner. In use, the balloon insert 10A is free-floating in the stomach compartment and unattached.

FIGS. 9-11 illustrate an alternate embodiment of the stomach tube similar to the levine tube but in this case a modified lavacuator tube 20A. Tube 20A has a longitudinal slit 32 extending from the inner end thereof upwardly a short distance about 2 to 5 inches. Pairs of small openings 34 are arranged on opposite sides of the slit 32, and a loop 36 extends through each pair of openings to provide an eyelet for reasons explained below.

In use, the deflated balloon, either 10 or 10A, is positioned inside tube 20A at the end thereof where the slit 32 is located, the insufflation tube 22 being attached to the balloon. Next, a drawstring 38 is threaded through the loops 34 in zig-zag fashion from the end of tube 20A upwardly and into the interior of the tube at the other end of the slit. The drawstring extends through the tube to the outer free end thereof, and when tensioned, it closes the tube at the slit. At the inner end of tube 20A, string 38 extends several times through the end loops 36 to thereby provide a mild resistance when the string is tensioned to close the slit. However, such end connection 40 must be loose enough whereby the string may be withdrawn from the loops when slightly more tension is applied.

After the assembled tube 20A is positioned inside the stomach 14, tension is applied to the outside free end of drawstring 38 to remove it from the eyelet loops 36 and thereby allow tube 20A to open at the slit 32. Next, air or another fluid is introduced into the balloon via the insufflation tube 22. As the balloon increases in size it spreads apart stomach tube 20A at the slit thereof, as shown in FIG. 11. When the balloon is fully inflated, insufflation tube 22 is easily detached by holding tube 20A and pulling on the free outside end of the insufflation tube. The balloon is urged against tube 20A but its inflated size prevents it from being drawn into the tube. Once the insufflation tube is detached, both it and the stomach tube are removed and the balloon freely floats in the stomach.

We claim:

1. A stomach insert for treating obesity in humans by reducing the stomach volume comprising a flexible, free-floating and unattached, inflatable balloon having a manufactured shape and significant resistance to over-inflation, the balloon being inflatable to its manufactured shape to a volume effective to reduce the stomach volume of a person being treated, and at least a portion of the balloon having self-sealing means to facilitate inflation of the balloon.

2. A stomach insert as in claim 1 wherein the balloon has an inflated volume of approximately 200 to 800 cc.

3. A method for treating obesity in humans comprising the steps of assembling a deflated stomach balloon with an insufflation tube releasably attached thereto inside a standard stomach tube, the balloon having a manufactured shape and significant resistance to over-inflation, thereafter introducing the stomach tube through the mouth and into the stomach, urging the balloon out of the stomach tube and into the stomach, inflating the balloon through the insufflation tube with a given amount of fluid to increase the volume thereof to its manufactured shape, releasing the insufflation tube from the inflated balloon thereby enabling the inflated balloon to freely float within the stomach, and then removing the stomach tube and the insufflation tube from the stomach and out through the mouth whereby the inflated balloon is unattached and free to float within the stomach.

4. A method as in claim 3 wherein the balloon is inflated to a volume approximately 80% of the stomach volume.

5. A method as in claim 3 including the step of removing the balloon from the stomach by introducing extraction means through the mouth and into the stomach, grasping and puncturing the balloon with the extraction means, and then withdrawing the deflated balloon out of the stomach and through the mouth.

6. A method as in claim 5 wherein the extraction means includes a fiberoptic gastroscope with needle biopsy forceps.

7. An assembly comprising a stomach tube having a longitudinal slit at one end thereof, a deflated stomach balloon inside the tube at the same end as the longitudinal slit, insufflation means releasably attached to the balloon and extending through the stomach tube, and drawstring means releasably closing the end of the stomach tube at the slit whereby upon removal of the drawstring means and inflation of the balloon the balloon is easily separated from the stomach tube as the tube spreads apart at the slit.

8. A stomach insert as in claim 1 wherein the self-sealing means to facilitate inflation of the balloon includes a self-sealing substance on the balloon to facilitate puncture thereof with insufflation means through which the balloon is inflated and to facilitate sealing of the puncture upon removal of the insufflation means.

9. A stomach insert as in claim 1 wherein the balloon is fabricated from polyurethane sheet material.

10. A stomach insert as in claim 1 wherein the balloon comprises a single layer.

11. A stomach insert as in claim 1 wherein the balloon includes a central opening extending therethrough.

12. A stomach insert as in claim 11 wherein the central opening in the balloon includes flared outer ends.

13. A stomach insert as in claim 12 wherein the balloon is fabricated from polyurethane sheet material.

* * * * *